United States Patent

Psaar

[11] 4,007,172
[45] Feb. 8, 1977

[54] DYESTUFF INCLUDING PYRIMIDO-INDOLE MOIETY

[75] Inventor: Hubertus Psaar, Leverkusen, Germany

[73] Assignee: Bayer Aktiengesellschaft, Leverkusen, Germany

[22] Filed: Mar. 2, 1976

[21] Appl. No.: 663,138

[30] Foreign Application Priority Data

Mar. 8, 1975 Germany ............... 2510238

[52] U.S. Cl. ............... 260/240.9; 260/251 H
[51] Int. Cl.² ............... C07C 487/04
[58] Field of Search ........ 260/240 D, 240.9, 251 A

[56] References Cited

UNITED STATES PATENTS

| | | | |
|---|---|---|---|
| 3,346,571 | 10/1967 | Spatz et al. | 260/240.9 X |
| 3,546,225 | 12/1970 | Paragamian | 260/251 A |
| 3,904,613 | 9/1975 | Schmitt | 260/240.9 X |

Primary Examiner—Allen B. Curtis
Attorney, Agent, or Firm—Plumley and Tyner

[57] ABSTRACT

The invention relates to compounds of the formula

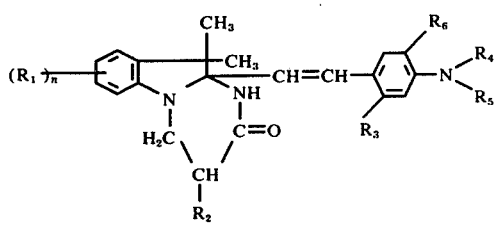

wherein
$R_1$ = hydrogen, halogen, alkyl, alkenyl, etc.
$R_2$ = hydrogen or alkyl,
$R_3$ = hydrogen, alkyl, alkoxy or halogen,
$R_4$ and $R_5$ = alkyl, alkenyl, cycloalkyl, aryl or aralkyl,
$R_6$ = hydrogen, alkyl or alkoxy and
$n$ = the numbers 1–4.

The compounds are outstanding suitable for transfer printing of acid-modified fiber materials.

6 Claims, No Drawings

DYESTUFF INCLUDING PYRIMIDO-INDOLE MOIETY

The invention relates to compounds of the general formula

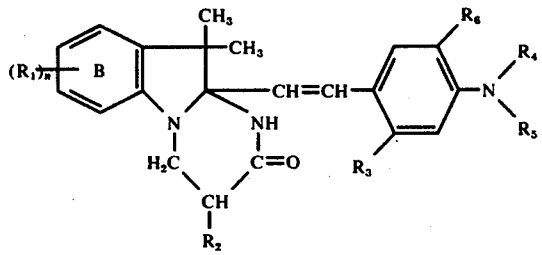

wherein
  $R_1$ denotes hydrogen, halogen, alkyl, alkenyl, cycloalkyl, carbalkoxy, cyano, nitro or alkoxy,
  $R_2$ denotes hydrogen or alkyl,
  $R_3$ denotes hydrogen, alkyl, alkoxy or halogen,
  $R_4$ and $R_5$ denote alkyl, alkenyl, cycloalkyl, aryl or aralkyl,
  $R_6$ denotes hydrogen, alkyl or alkoxy and $n$ denotes the numbers 1–4,
  it being possible for the abovementioned alkoxy and hydrocarbon radicals optionally to contain non-ionic substituents,
as well as a process for their preparation and their use as dyestuff-forming agents.

Suitable non-ionic substituents are substituents which are customary in dyestuff chemistry and which do not have a substantial influence on the sublimation properties of the base molecule, such as alkyl, alkoxy, halogen, cyano and the like.

Suitable alkyl and alkenyl radicals are those with 1–4 and 2–4 C atoms respectively. The alkyl radicals can preferably carry a further non-ionic substituent, such as Cl, CN, OH, $OCH_3$, $OC_2H_5$ or acetoxy. The $CF_3$ group is also possible. Methyl and ethyl are preferred.

Suitable aryl radicals are, above all, phenyl radicals, which preferably can be monosubstituted to trisubstituted by $C_1$–$C_4$-alkyl, $C_1$–$C_4$-alkoxy, Cl or $CF_3$. $C_3$–$C_4$-alkyl or alkoxy groups which may be present are preferably in the p-position.

Suitable aralkyl radicals are phenyl-$C_1$–$C_3$-alkyl radicals, which can be substituted in the phenyl nucleus as described above. Benzyl and phenylethyl are preferred.

Suitable cycloalkyl radicals are 5-membered to 7-membered and can be monosubstituted to trisubstituted by $CH_3$ or Cl. Cyclohexyl is preferred.

Suitable alkoxy radicals are those with 1 to 4 C atoms. Methoxy and ethoxy are preferred.

Preferably, $n$ represents 1, $R_1$ is in the 5-position of ring B and $R_6$ represents hydrogen.

Halogen is understood preferably as Cl and Br.

Preferred compounds of the formula I are those of the general formula

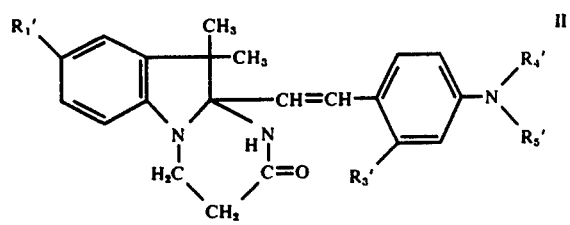

wherein
  $R_1'$ denotes hydrogen, methyl, ethyl, chlorine, cyano, methoxy or ethoxy,
  $R_3'$ denotes hydrogen, chlorine or methyl and
  $R_4'$ and $R_5'$ denote methyl, ethyl, phenyl, benzyl, cyanoethyl, chloroethyl, methoxyethyl or ethoxyethyl.

The compounds of the formula I can be prepared by reacting compounds of the formula

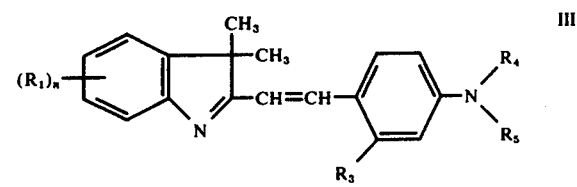

wherein
  $R_1$ to $R_5$ and $n$ have the abovementioned meaning, with acrylic acid amides of the formula

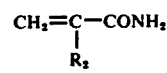

in an acid medium, the indole nitrogen being quaternised, and subsequently closing the lactam ring by adding alkali.

A one-pot process for the preparation of the substances according to the invention, which consists in condensing compounds of the formula

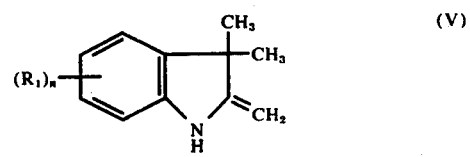

or

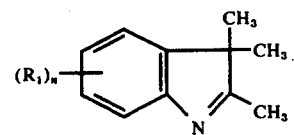

wherein
  $R_1$ and $n$ have the abovementioned meaning, with aldehydes of the formula

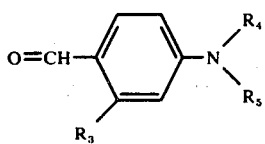

wherein $R_1$ to $R_5$ and $n$ have the abovementioned meaning, and then reacting the compound of the formula III, without intermediate isolation thereof, with acrylic acid amides of the formula IV and subsequently effecting closure of the lactam ring by adding alkali, is particularly advantageous.

The reaction of III with IV is carried out in the presence of customary organic or preferably inorganic acids in which the compounds of the formula III dissolve. Suitable acids are sulphuric acid, hydrochloric acid, phosphoric acid and acetic acid, which optionally . . . by water and/or water-miscible organic solvents, such as methanol, ethanol, isopropanol, acetonitrile, dimethylamine and others.

The reaction temperatures can be varied within a relatively wide range. In general, the reaction is carried out at 0° to 120° C.

Condensing agents which can be used for the reaction of V with VI are the customary agents which eliminate water, such as acetic anhydride and propionic anhydride. In this case the reaction temperatures are from 80° to 120° C.

Closure of the lactam ring is . . . by customary alkaline agents, such as alkali metal hydroxides and alkaline earth metal hydroxides and alkali metal carbonates. NaOH and KOH are preferred.

In general, the compounds of the formula I precipitate in a solid form when alkali is added, so that these compounds can be isolated by simple filtration.

A further process for the preparation of the compounds of the formula I is characterised in that compounds of the formula VII

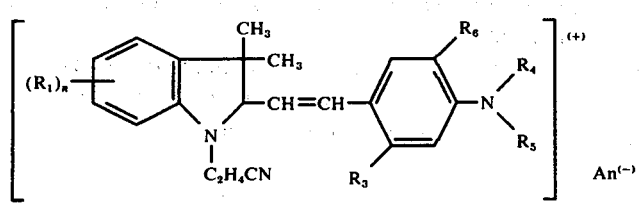

wherein $R_1$ to $R_6$ and $n$ have the abovementioned meaning and $An^{(-)}$ denotes an anion, are treated with concentrated sulphuric acid at 0°–30° C and the reaction mixture is then rendered neutral or alkaline with alkali in order to close the lactam ring.

The compounds of the formulae III, V, VI and VII are known or are readily obtainable according to known methods. (Compare U.S Pat. Nos. 2,280,253 and 2,179,895, German Patent Specification No. 891,120 and BIOS No. 1,661,43). Suitable compounds of the formula V are: 2,3,3-trimethyl-indolenine, 2,3,3-trimethyl-5-chloro-indolenine, 2,3,3-trimethyl-5-methyl-indolenine, 2,3,3-trimethyl-5cyano-indolenine, 2,3,3-trimethyl-5-tert.-butyloxy-indolenine and 2,3,3-trimethyl-5-carbomethoxy-indolenine.

Suitable compounds of the formula VI are: 4-(N,N-dimethyl)-benzaldehyde, 4-(N,N-dibenzyl)-benzaldehyde, 4-(N,N-chloroethyl)-benzaldehyde, 2-methyl-4-(N,N-diethyl)-benzaldehyde and 2-chloro-4-(N,N-diphenylethyl)-benzaldehyde.

The new compounds I are dye-forming agents which are suitable for printing acid-modified textile materials by the transfer printing process or for recording materials, such as, for example, heat-sensitive copying papers, hectographic printing papers or pressure-sensitive copying papers.

The compounds according to the invention are soluble in or miscible with substances of high molecular weight, such as, for example, animal, vegetable or mineral waxes, ethyl cellulose, polyvinyl acetate or alhyd resins, and dissolve in organic solvents, such as, for example, methanol, ethanol, chloroform, benzene, toluene, chlorobenzenes, ethylnaphthalenes and the like. Solutions of the new compounds in the abovementioned solvents develop a red to violet colour immediately after the solutions have been absorbed on activated clay substances. These activated clay substances are, for example, acid clay, attapulzite, zeolite and bentonite, solid organic acids, such as succinic acid, maleic acid, tamic acid or benzoic acid, or acid polymers, such as, for example, carboxypolyethylene, phenol-aldehyde polymers or styrene-maleic anhydride copolymers with acid groups.

The dye-forming agents of the formula II are particularly suitable for transfer printing.

In general, the dye-forming agents are applied to the temporary support not as such but with the aid of printing pastes, spray solutions or dye liquors and preferably of printing pastes having a neutral reaction, in a manner which is in itself known.

These printing pastes are characterised in that they contain at least a. a dyestuff-forming agent of the formula I or II which can be sublimed at 160° to 240° C, b. a neutral organic solvent which is customary for printing inks and c. a thickener or binder which is soluble in the solvent.

Suitable solvents, in addition to water, are neutral organic solvents, that is to say organic solvents which do not react chemically with the dyestuff-forming agents, for example hydrocarbons, such as benzene, toluene or xylene; chlorinated hydrocarbons, such as chlorobenzene, ethylene chloride, trichloroethylene and tetrachloroethylene; alcohols, such as methanol, ethanol, isopropanol, butanol or benzyl alcohol; glycols; ketones, such as methyl ethyl ketone or cyclohexanone, as well as various ethers and esters.

They are used in the pure form or as mixtures. Preferred solvents are the hydrocarbons mentioned and amongst these, in turn, toluene as well as ethanol and glycol are preferred.

In principle, the thickeners and binders which can be employed are those of the same types as are used for the production of transfer printing inks based on disperse dyestuffs, with the proviso, because of the sensitivity of the dyestuffs, to be used according to the invention, to acid and alkali, that the resins have a neutral reaction.

Preferred thickeners and binders are polyvinyl alcohols, polyvinyl acetates, carob bean flours and derivatives thereof, guar flours and derivatives, cellulose esters and cellulose ethers or mixtures thereof. The solvents used are those in which the abovementioned thickeners and binders dissolve or swell.

The printing inks can be applied to the temporary support by the various processes customary in paper printing and coating, such as roller printing, rotary printing and flat-bed film printing or photogravure, flexographic printing, screen printing and offset printing. The printing inks can also be applied by means of a coating knife or with a padder and also by means of spray guns or paint brushes.

It is sometimes also disadvantageous when, in addition to the said basic dyestuffs, disperse dyestuffs which can be sublimed, such as, for example, Disperse Red 4, 11 and 15 and Disperse Violet 1 and 4, are incorporated into the printing pastes, because, in this way, it is possible somewhat to improve the fastness to light of dyeings, which is sometimes only moderate when pure basic dyestuffs are used.

The disperse dyestuff content makes up 1 to 90% of the total dyestuff content of the printing inks.

The addition of substances having an alkaline reaction (0.1–100% by weight relative to the dye-forming agent) is also advisable since the papers frequently contain acids which, with dye-forming agents, form salts which cannot be sublimed.

Substances having an alkaline reaction which can be used are both those compounds which display the required alkaline reaction under normal conditions and those compounds which produce an alkaline reaction only at elevated temperatures, that is to say at temperatures from 50° to 200° C, due to decomposition.

Examples which may be mentioned are: alkali metal hydroxides and alkaline earth metal hydroxides, alkali metal carbonates and alkaline earth metal carbonates, alkali metal bicarbonates and alkaline earth metal bicarbonates, alkali metal salts and alkaline earth metal salts of weak acids, especially carboxylic acids, such as formic acid and acetic acid, alkali metal alcoholates and alkaline earth metal alcoholates as well as alkaline earth metal oxides and aluminum oxides.

Preferred agents having an alkaline reaction are sodium methylate and sodium ethylate (in the case of anhydrous printing inks) as well as NaOH, KOH, sodium carbonate, $K_2CO_3$ and calcium oxide in the case of aqueous printing inks.

The preferred temporary support is paper, the grade of which is determined by the nature of the printing ink and the printing process. In addition, cellophane, cellulose textiles, metal foils (especially aluminium foils) and the like are also suitable.

Transfer printing from the temporary support to the substrate is carried out in a manner which is in itself known at 160° to 230° C. Suitable substrates are, above all, customary textile materials which can be dyed with basic dyestuffs, such as, for example, textile materials made of polyacrylonitrile, of copolymers of acrylonitrile with other vinyl compounds, such as vinyl chloride, vinylidene chloride, vinyl fluoride, vinyl acetate, vinylpyridine, vinylimidazole and vinyl alcohol, acrylic acid esters and amides and methacrylic acid esters and amides and as-dicyanoethylene, and those made of acid-modified polyamide fibres and acid-modified polyester fibres. Acid-modified aromatic polyesters are, for example, polycondensation products of sulphoterephthalic acid and ethylene glycol, that is to say polyethylene glycol terephthalates containing sulphonic acid groups (of the type of DACRON 64 from Messrs. E. I. Du Pont de Nemours and Company), such as are described and U.S. Pat. No. 2,893,816.

In addition, other types of fibres, for example tannin-treated cotton, leather and the like, are also suitable.

The dyestuff transfer is effected at temperatures from 160° to 240° C, preferably 200° to 220° C, in the course of 15 to 60 seconds.

Heat transfer can be effected by direct contact with heating plates, by hot air, superheated steam or infra-red radiation. Dyeings and prints which have good fastness properties in use are obtained on the materials used as the substrates.

In the examples "parts" denotes parts by weight.

EXAMPLE 1

59.6 parts of 4-dimethylaminobenzaldehyde and 63.6 parts of 2,33-trimethylindolenine are heated in 400 parts of glacial acetic acid and 25 parts of acetic anhydride for 1 hour at 90° C. 210 parts of acrylic acid amide and 25 parts of concentrated hydrochloric acid are then added and the mixture is stirred for 10 hours at 110°–115° C. The solution is introduced into 4,000 parts of ice water and 800 parts of sodium hydroxide solution. The reaction product which has precipitated is filtered off and dried in vacuo at 60° C; it has the formula

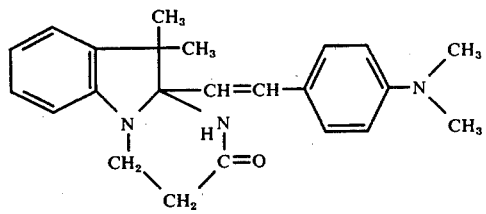

A

A solution in toluene gives a bluish-tinged red dyeing on acid clay.

If 2,3,3-trimethyl-5-chloroindolenine is used in place of 2,3,3-trimethylindolenine, a product of the formula

B which also gives a bluish-tinged red dyeing on acid clay is obtained.

The following compounds were prepared analogously to Example 1:

| Lactam | | Colour shade on acid clay |
|---|---|---|
| C | 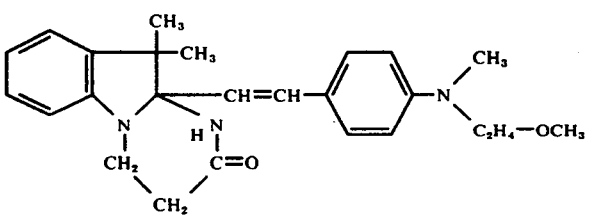 | bluish-tinged red |
| D | 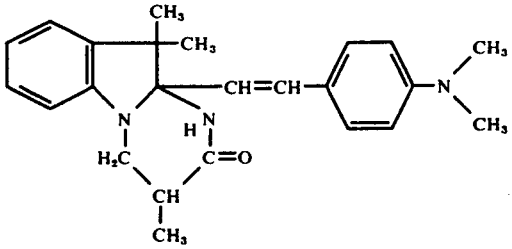 | bluish-tinged red |
| E | 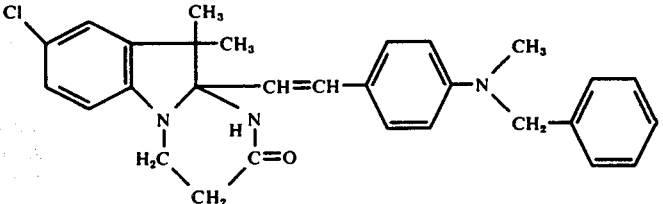 | bluish-tinged red |
| F | 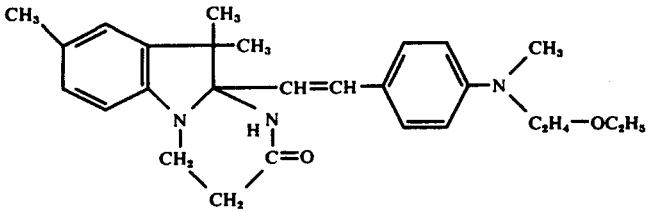 | bluish-tinged red |
| G | 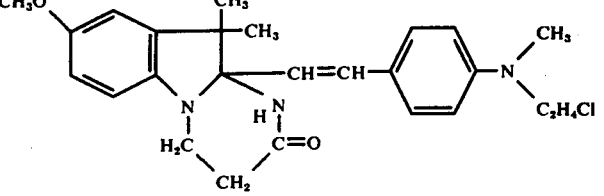 | pink |
| H | 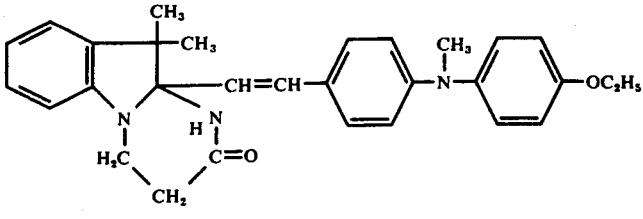 | violet |
| I | 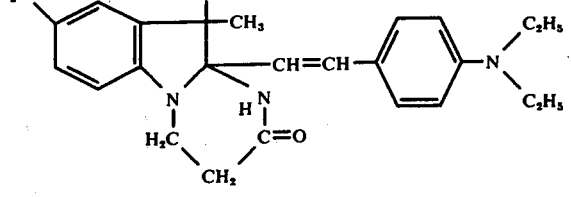 | violet |

-continued

| Lactam | Colour shade on acid clay |
|---|---|
| 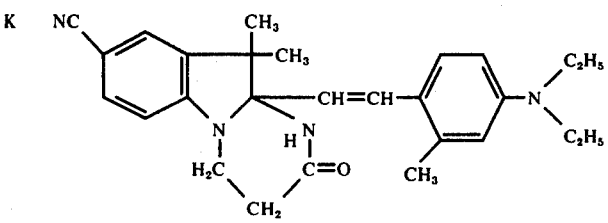 K | violet |

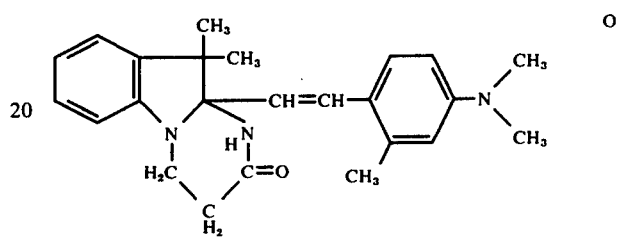 O is obtained.

EXAMPLE 2

50 parts of the dyestuff of the formula

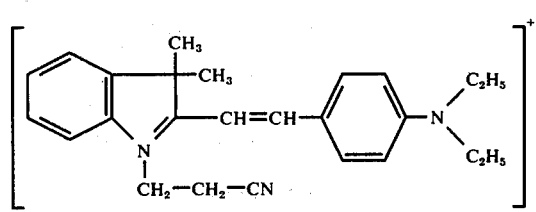 L were dissolved in 100 parts of concentrated sulphuric acid at 20°–30° C and the solution was stirred for 15 hours at room temperature. The solution was poured onto 400 parts of ice and the lactam was precipitated with concentrated sodium hydroxide solution.

It has the formula

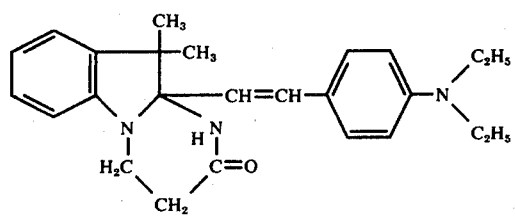 M

A bluish-tinged red print is obtained by transfer printing on a fabric made of polyacrylonitrile fibres.

If a dyestuff of the formula

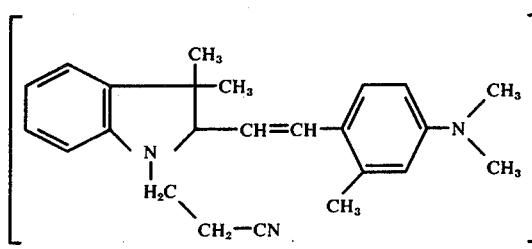 N is used in place of the dyestuff of the formula L, a lactam of the formula

EXAMPLE 3

100 parts of the compound of the formula

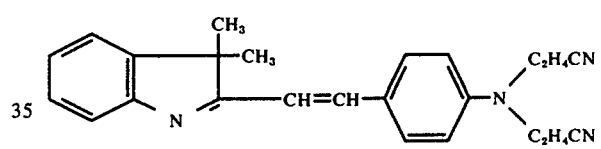 P were stirred in 400 parts of glacial acetic acid and 25 parts of concentrated hydrochloric acid with 200 parts of acrylic acid amide for 6 hours at 110° C. The solution was poured into 3,000 parts of ice water and the lactam was precipitated with concentrated sodium hydroxide solution. It has the formula

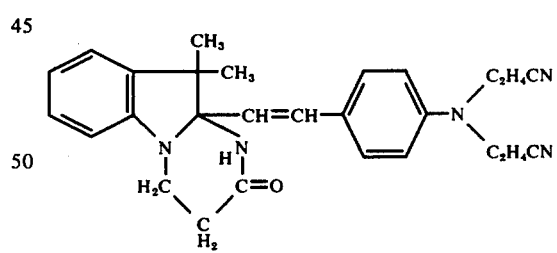 Q

A solution of the compound in toluene gives a scarlet dyeing on acid clay.

If a compound of the formula

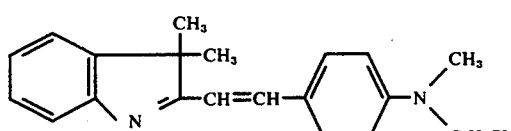 R is used in place of the compound of the formula P, a lactam is obtained which, when dissolved in toluene, develops a red colour on a phenol-aldehyde copolymer.

EXAMPLE 4

60 parts of the compound of the formula A are introduced into a solution consisting of

| | |
|---|---|
| 100 | parts of ethylene glycol |
| 820 | parts of denatured ethanol |
| 40 | parts of N 22 ethylcellulose and |
| 10 | parts of sodium methylate |
| 1,000 | parts | and the mixture is homogenised or brought into solution in a ball mill or funnel mill.

This paste is now spread by hand using a doctor blade onto a paper with a weight per square metre of between 60 and 90 g and a Cobb value which is also between 60 and 90.

The paper is dried. On heat transfer printing onto a polyacrylonitrile fabric (PAC) at 200° C for 30 seconds, a deep red print with good fastness to wet processing and light is obtained with this paper. Even when the paper is stored for several weeks before transfer printing, an equally deep print of equal depth of colour is obtained under the conditions described above.

EXAMPLE 5

60 parts of a compound of the formula B

| | |
|---|---|
| 20 | parts of p-hydroxydiphenyl polyglycol ether |
| 370 | parts of water and |
| 50 | parts of sodium hydroxide solution of 38° Be strength |
| 1,000 | parts | are triturated in a ball mill and 1,000 parts of a thickener, which consists of a 10% strength paste produced by swelling an ether of carob bean flour in water are then introduced.

A temporary support, for example a cotton nettle, is printed with the printing paste thus obtained according to one of the methods customary in textile printing and dried and heat transfer printing is carried out as described in Example 4.

A clear bluish-tinged red shade with good fastness to light and wet processing is obtained on a PAC fabric even when the cotton temporary support has been stored for several weeks.

EXAMPLE 6

A mixture consisting of

| | |
|---|---|
| 30 | parts of chlorinated rubber solution (52% in toluene) |
| 5 | parts of solvent-free medium oil alkyd resin |
| 3 | parts of dibutyl phthalate |
| 48 | parts of toluene |
| 10 | parts of the compound of the formula G and |
| 4 | parts of sodium methylate |
| 100 | parts | is homogenised in a ball mill and then printed on an aluminum foil by the gravure printing process and the foil is dried.

Transfer printing onto a polyacrylonitrile fabric is carried out as described in Example 4.

A pink print with good fastness properties is obtained.

EXAMPLE 7

A printing paste prepared by mixing (1:2) the printing inks X and Y, described below, is printed onto paper by rotary screen printing or roller printing, colour patterns with outstanding sharpness of outline being obtained.

Using the papers printed in this way, heat transfer printing (30 seconds at 200° C) onto acid-modified polyamide or polyacrylonitrile gives a clear red print with good fastness properties, especially with good fastness to light.

Preparation of printing ink X 500 g of a homogenised dyestuff dispersion (consisting of 60 g of C.J. Disperse Red 15, 6 g of 3-benzyl-4-hydroxy-biphenyl polyether and 434 g of water) are mixed intimately with 500 g of a thickener (consisting of 140 g of heavy petroleum spirit, 2.5 g of aluminum stearate, 22.5 g of nonylphenol polyglycol ether and 110 g of a copolymer of ethylene and maleic anhydride (1:1) (for example EMA$^{(R)}$-91 from Monsanto) and 450 g of 14.5% strength ammonia (introduced with cooling).

Preparation of printing ink Y 500 g of a homogenised dyestuff dispersion (consisting of 60 g of the dyestuff of the formula A, 6 g of 3-benzyl-4-hydroxy-bis-phenyl polyglycol ether and 434 g of water) are mixed with 500 g of the thickener described above (which additionally also contains 10 g of triethanolamine).

The printing ink prepared in this way can be mixed with printing ink X or can be printed as such onto papers, which are then suitable as temporary supports for transfer printing of polyacrylonitrile.

EXAMPLE 8

20 g of the compound of the formula Q are ground in a bead mill with 0–7.5 g of a cyclohexanone-formaldehyde resin with a softening point above 160° C and 10–2.5 g of $N_4$ ethyl-cellulose. 100 parts of a printing ink are prepared by adding toluene, which contains 10% of polywaxes. A paper is impregnated with this printing ink using a spray gun. When this paper is pressed with a textile of polyacrylonitrile fibres for 15–30 seconds at 180° C a scarlet print with good fastness properties is obtained. If a textile of acid-modified polyester fibres (Dacron 64) is used, a deep scarlet dyeing is again obtained.

I claim:
1. Compounds of the formula

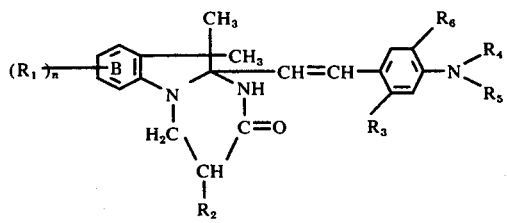

wherein
$R_1$ denotes hydrogen, halogen, alkyl, alkenyl, cycloalkyl, carbalkoxy, cyano, nitro or alkoxy,
$R_2$ denotes hydrogen or alkyl,
$R_3$ denotes hydrogen, alkyl, alkoxy or halogen, $R_4$ and $R_5$ denote alkyl, alkenyl, cycloalkyl, aryl or aralkyl, $R_6$ denotes hydrogen, alkyl or alkoxy and $n$ denotes the numbers 1–4, it being possible for the abovementioned alkoxy and hydrocarbon radicals optionally to contain non-ionic substituents.

2. Compounds according to claim 1, wherein $n$ represents the number 1 and $R_6$ represents hydrogen and the radical $R_1$ is in the 5-position of ring B.

3. Compounds according to claim 1 of the formula wherein
- $R_1'$ denotes hydrogen, methyl, ethyl, chlorine, cyano, methoxy or ethoxy,
- $R_3'$ denotes hydrogen, chlorine or methyl and
- $R_4'$ and $R_5'$ denote methyl, ethyl, phenyl, benzyl, cyanoethyl, chloroethyl, methoxyethyl or ethoxyethyl.

4. Compound according to claim 1 of the formula

5. Compound according to claim 1 of the formula

6. Compound according to claim 1 of the formula

* * * * *